(12) United States Patent
Yu

(10) Patent No.: US 10,687,895 B2
(45) Date of Patent: Jun. 23, 2020

(54) INTEGRATED FIBER OPTIC PROBE FOR PERFORMING IMAGE-GUIDED LASER INDUCED THERMAL THERAPY

(71) Applicant: Bing Yu, Hudson, OH (US)

(72) Inventor: Bing Yu, Hudson, OH (US)

(73) Assignee: THE UNIVERSITY OF AKRON, Akron ( * ) Notice: Subject to any disclaimer, the term of this patent is extended or adjusted under 35 U.S.C. 154(b) by 825 days.

(21) Appl. No.: 15/330,808

(22) Filed: Nov. 7, 2016

(65) Prior Publication Data

US 2017/0128132 A1 May 11, 2017

Related U.S. Application Data

(60) Provisional application No. 62/251,757, filed on Nov. 6, 2015.

(51) Int. Cl.
| | |
|---|---|
| *A61B 6/00* | (2006.01) |
| *A61B 18/22* | (2006.01) |
| *A61B 5/00* | (2006.01) |
| *A61B 5/01* | (2006.01) |
| *A61B 5/055* | (2006.01) |
| *A61B 18/00* | (2006.01) |

(52) U.S. Cl.
CPC ............ *A61B 18/22* (2013.01); *A61B 5/0075* (2013.01); *A61B 5/01* (2013.01); *A61B 5/055* (2013.01); *A61B 2018/00577* (2013.01); *A61B 2018/00773* (2013.01); *A61B 2018/00791* (2013.01); *A61B 2018/2211* (2013.01)

(58) Field of Classification Search
CPC ..................................................... A61B 5/00
See application file for complete search history.

(56) References Cited

U.S. PATENT DOCUMENTS

| | | | | |
|---|---|---|---|---|
| 6,138,046 | A * | 10/2000 | Dalton | A61N 5/0601 356/300 |
| 2009/0043296 | A1* | 2/2009 | Foster | A61B 5/0059 606/11 |
| 2011/0112435 | A1* | 5/2011 | Ramanujam | A61B 5/0071 600/567 |
| 2014/0288542 | A1* | 9/2014 | Torchia | A61B 18/22 606/12 |
| 2015/0141768 | A1* | 5/2015 | Yu | A61B 5/0084 600/301 |

OTHER PUBLICATIONS

Ritz et al; Continuous Changes in the Optical Properties of Liver During Laser-Induced Interstitial Thermotherapy; Lasers in Surgery and Medicine 28:307-312 (2001).

(Continued)

*Primary Examiner* — Joel F Brutus
(74) *Attorney, Agent, or Firm* — Renner Kenner Greive Bobak Taylor & Weber

(57) ABSTRACT

A fiber optic probe includes a first diffuse reflectance spectroscopy fiber, a second diffuse reflectance spectroscopy fiber, and a temperature sensor at a distal end of a temperature sensor fiber. Other embodiments further include a treatment fiber for delivering a high optical power density of light to a tumor and a dosimetry fiber for monitoring the light flux of the treatment fiber. Other embodiments utilize an image-guidance step in a method of using the fiber optic probe.

20 Claims, 4 Drawing Sheets

(56) References Cited

OTHER PUBLICATIONS

Tosi et al; Fiber-optic combined FPI-FBG sensors for monitoring of radiofrequency thermal ablation of liver tumors: ex vivo experiments; Applied Optics / vol. 53, No. 10 / Apr. 1, 2014.
Buttemere et al; In vivo assessment of thermal damage in the liver using optical spectroscopy; Journal of Biomedical Optics 9(5), 1018-1027 (Sep./Oct. 2004).
Hsu et al; Liver tumor gross margin identification and ablation monitoring during liver radiofrequency treatment; J Vasc Interv Radiol 2005; 16:1473-1478.
Ritz et al; Optical properties of native and coagulated porcine liver tissue between 400 and 2400 nm; Lasers in Surgery and Medicine 29:205-212 (2001).

\* cited by examiner

INTEGRATED FIBER OPTIC PROBE FOR PERFORMING IMAGE-GUIDED LASER INDUCED THERMAL THERAPY

CROSS-REFERENCE TO RELATED APPLICATION

The present application claims priority to U.S. Provisional Patent Application No. 62/251,757, filed Nov. 6, 2015, incorporated herein by reference.

FIELD OF THE INVENTION

Embodiments of the present invention relate to a fiber optic probe. Embodiments of the present invention relate to a fiber optic probe capable of monitoring a thermal ablation procedure. Embodiments of the present invention relate to a fiber optic probe capable of both performing a thermal laser ablation procedure and monitoring the thermal laser ablation procedure. Embodiments of the present invention relate to a method of using a plurality of fiber optic probes at different positions for optimal performance and monitoring of a thermal ablation procedure.

BACKGROUND OF THE INVENTION

Thermal ablation is a minimally invasive surgical procedure that has been widely used in treating a variety of inoperable tumors and tumor beds. In thermal ablation, radiative, cryogenic, electrical or acoustic energy is delivered through an applicator to a predetermined location(s) inside a target tumor to induce high temperature that causes irreversible cell injury, leading to apoptosis and eventually coagulative necrosis of the cancer cells. The degree of tissue coagulation or damage depends on both the temperature and the duration of the heating process, as well as the tissue composition.

Thermal therapy creates three different zones of hyperthermic ablation in the target tissue. The first zone (Zone 1), which generally includes the area surrounding the applicator tip or central zone, undergoes coagulative necrosis at temperatures ≥50° C. In Zone 1, protein denaturation, enzyme inactivation, cell membrane rupture, mitochondrial injury, hyperchromasia, and at higher temperatures (e.g. >100° C.), tissue vaporization and carbonization also occur. The area away from the applicator tip with a temperature from 41° C. to 45° C. is called the transitional zone (Zone 2). In Zone 2, the heat-injury to the cells is sub-lethal at such temperatures and is often reversible. The tissue beyond Zone 2 (Zone 3) serves as a heat-sink to the other zones due to the blood flows, and thus has decreased ablation efficacy.

The temperature distribution in the tissue is a function of multiple factors, including the energy delivered, energy-to-heat converting efficiency, thermal conductivity, and perfusion of the tissue. An effective treatment should completely coagulate the whole tumor without tissue charring (i.e., the tumor mass is 100% included in Zone 1), while minimizing damages to the normal tissue on the tumors margins (i.e., maintain the margins in Zone 2). Multiple applicators are often required for an efficient and precise ablation, depending on the size and shape of the tumor.

Common types of energy used in thermal ablation are radiofrequency (RF), microwave, high-intensity focused ultrasound (HIFU), and laser.

Radiofrequency ablation (RFA) has been used in numerous solid organ malignancies and is now a part of standard therapy in several tumors including hepatocellular carcinoma. In RFA, a high frequency alternating electric current is applied to the target tissue using RF electrodes (unipolar or bipolar, single or multi-tined). The varying direction of the electric current causes molecular friction due to ionic agitation resulting in tissue heating up to 100° C. However, for temperature >100° C. the tissue electrical impedance increases, limiting the flow of electric current to the remaining part of the target tissue.

Microwave ablation (MWA) uses antennas to apply electromagnetic waves between 900 to 2500 MHz to the target tissue, which generates heat in the target tissue through the process of dielectric hysteresis (rotating dipoles). MWA techniques are more efficient for ablating tissues with high water content (solid organs and tumors) and temperatures >100° C. can be achieved during ablation.

In HIFU ablation, ultrasound energy is focused to the target tumor to generate temperatures up to 60° C. The acoustic pressure waves cause expansion and relaxation of gaseous nuclei within the cells, leading to the collapse of the cell and nuclear membranes, the mitochondria and the endoplasmic reticulum.

Laser-induced thermal therapy (LITT) generally employs a flexible optical fiber or a diffuser attached to the tip of an optical fiber to deliver high power laser (800-1064 nm) to the target tumor. The tissue temperature increases due to light absorption, dominantly by blood. The size of the thermally induced necrosis formed due to laser coagulation can exceed the light penetration depth since part of the energy that is a function of the temperature gradient diffuses into the surrounding colder tissues. The heat generated due to the local absorption of light depends on the fluence rate (W/cm$^2$), the tissue absorption and scattering properties, as well as the thermal conductivity of the tissue. Since tissue optical properties are wavelength dependent, the ablation volume for a given tumor varies depending on the laser ablation wavelength. While it is challenging to compare the existing thermal ablation techniques, LITT has the unique feature of being able to treat multi-focal diseases while also being compatible with magnetic resonance imaging (MRI) and computed tomography (CT), which are widely used for cancer detection and imaging-guidance during surgeries and thermal ablation procedures. LITT, coupled with imaging (e.g., MRI, CT, and ultrasound) has been successfully demonstrated in a number of studies for treating surgically challenging tumors in the brain, prostate, head and neck, liver, lung, kidney, breast, and bone.

Irrespective of the technique used for tumor ablation, imaging and real-time monitoring of temperature distribution and tissue response are critical for an effective and safe therapy. Image-guidance assists in the precise placement of the treatment probe(s) so that an optimal temperature distribution can be obtained across the whole tumor mass. Imaging (e.g. MRI, CT, and ultrasound) has also been utilized to evaluate the response of tumor to the thermal ablation. Temperature elevation is often monitored during ablation procedures and is used as a feedback to control the thermal dosage. An optimal temperature distribution ensures complete destruction of tumor mass, thus reducing recurrence rate, while avoiding tissue charring and excessive damage to normal tissue and critical structures. Temperatures can be monitored invasively or noninvasively. Invasive methods involve the insertion of thermocouples or fiber optic temperature sensors to provide point measurements. Multiple invasive sensors may be required to obtain a coarse temperature map about the tumor under treatment.

In contrast, noninvasive methods can obtain a temperature distribution within the target tissue without any insertions.

Magnetic resonance thermometry (MRT) is one of the few noninvasive options for temperature monitoring during thermal ablation, especially in laser ablation due to its MRI compatibility. MRT is based on T1-relaxation or proton resonance frequency (PRF). Recently, the accuracy and temporal resolution of MRT has been evaluated in vitro. This generally concluded that the speed and accuracy of MRT was sufficient for controlling the thermal dosage for tumor ablation. However, both the T1-weighted and PRF-based MRT are tissue-type dependent. The T1-relaxation is affected by the presence of lipid (fat) molecules, so lipid/fat suppression techniques are often incorporated to minimize such effects. On the other hand, PRF is severely affected by microbubbles (created during ablation) and motion artifacts.

Recently, CT-based thermometry (CTT) has also been investigated for thermal ablation monitoring. The influence of some CT scan parameters on the standard deviation of CT numbers was analyzed. These studies indicated that the standard deviations of CT numbers decreased with an increase in tube current-time product, tube voltage and slice thickness, and with the decrease of collimation thickness. The temperature dependence of these parameters could be used to assess the target tissues at certain temperatures. However, the use of CT-thermometry for ablation monitoring is still in its infancy and may require further in vivo studies for improving the standard deviation of CT numbers in the region of interest. Moreover, CT utilizes ionizing radiation for monitoring which makes it a less attractive technique.

Compared to CTT and MRT, ultrasound monitoring techniques otter the benefits of being portable and less expensive, while also not making use of any ionizing radiation. Tissue heating changes the ultrasound propagation speed and attenuation in the tissue consequently changing the acoustic properties of the tissue. Such heat-induced changes in the target tissue induce time and frequency shifts in the backscattered echo signals. The propagation speed is independent of the tissue coagulation and the attenuation coefficient depends on effects due to tissue coagulation and temperature elevation. Therefore, temperature maps can be reconstructed from the backscattered echo signals. However, ultrasound images are affected by microbubbles that occur in tissues for temperatures >100° C., thus the maximum temperature that can be measured is limited to 100° C.

Among the existing monitoring techniques, MRT is the most commonly used in MRI-guided LITT procedures, especially for the treatment of brain tumors. A temperature accuracy of ±1° C. and a spatial resolution of ±1-2 mm can be achieved with MRT. However, MRI and MRT guided LITT require expensive equipment. The size of the MRI/MRT equipment also limits its use in smaller operation rooms and at remote sites. In addition, MRT and other noninvasive temperature-monitoring techniques use an indirect approach to measure the tissue temperature. These techniques only measure changes in the temperature-dependent tissue properties which are assumed to have changed linearly with temperature. Moreover, MRT, although in some ways superior to both CT and ultrasound, is unable to highlight the destroyed areas during the irradiation procedure directly. The coagulation state of the tissue is usually estimated based on the temperature data. Since different tissue types could coagulate at different temperatures, termination of the treatment based on a critical temperature value alone may lead to incomplete ablation and consequently increase the risk for recurrence.

Therefore, there is a clinical need for a noninvasive or minimally invasive LITT device that can simultaneously ablate the tumor mass and measure the tissue temperature and degree of tissue damage during a laser ablation procedure.

SUMMARY OF THE INVENTION

In a first embodiment, the present invention provides a fiber optic probe comprising a first diffuse reflectance spectroscopy fiber, a second diffuse reflectance spectroscopy fiber, and a temperature sensor fiber, said temperature sensor fiber having a temperature sensor at a distal end thereof.

In a second embodiment, the present invention provides a fiber optic probe as in the first embodiment, further comprising a treatment fiber for delivering a high optical power density of light to a tumor.

In a third embodiment, the present invention provides a fiber optic probe as in either the first or second embodiment, further comprising a dosimetry fiber for monitoring the light flux of said treatment fiber.

In a fourth embodiment, the present invention provides a fiber optic probe as in any of the first through third embodiments, wherein said first diffuse reflectance spectroscopy fiber is a source fiber operatively coupled with a light source in order to provide light from said light source to a tumor, wherein at least some of the light is reflected by the tumor, and wherein said second diffuse reflectance spectroscopy fiber is a detection fiber for detecting the reflected light.

In a fifth embodiment, the present invention provides a fiber optic probe as in any of the first through fourth embodiments, wherein said light source is a white light-emitting-diode and wherein said second diffuse reflectance spectroscopy fiber is operatively coupled with a spectrometer for calculating the reflected light detected by said second diffuse reflectance spectroscopy fiber.

In a sixth embodiment, the present invention provides a fiber optic probe as in any of the first through fifth embodiments, wherein said first diffuse reflectance spectroscopy fiber, said second diffuse reflectance spectroscopy fiber, said temperature sensor fiber, said treatment fiber, and said dosimetry fiber are optical fibers.

In a seventh embodiment, the present invention provides a fiber optic probe as in any of the first through sixth embodiments, further comprising a protective cable housing at least a portion of said first diffuse reflectance spectroscopy fiber, said second diffuse reflectance spectroscopy fiber, said temperature sensor fiber, said treatment fiber, and said dosimetry fiber, said protective cable extending into a distal end covering housing a distal end of said first diffuse reflectance spectroscopy fiber, said second diffuse reflectance spectroscopy fiber, said temperature sensor fiber, said treatment fiber, and said dosimetry fiber.

In an eighth embodiment, the present invention provides a fiber optic probe as in any of the first through seventh embodiments, said distal end covering being in the shape of a needle and being made from stainless steel.

In a ninth embodiment, the present invention provides a fiber optic probe as in any of the first through seventh embodiments, said distal end covering including a rounded distal end and being made from biocompatible epoxy.

In a tenth embodiment, the present invention provides a system comprising the fiber optic probe as in any of the first through ninth embodiments, wherein said first diffuse reflectance spectroscopy fiber and said second diffuse reflectance spectroscopy fiber are operatively coupled with a diffuse reflectance spectroscopy spectrometer, said temperature sensor fiber is operatively coupled with an optical sensing interrogator, said treatment fiber is operatively coupled with a treatment laser, and said dosimetry fiber is operatively coupled with a dosimetry detector.

In an eleventh embodiment, the present invention provides a system as in the tenth embodiment, further comprising a computer operatively coupled with said treatment laser, said optical switch, said dosimetry detector, said optical sensing interrogator, and said DRS spectrometer.

In a twelfth embodiment, the present invention provides a system as in either of the tenth or eleventh embodiments, wherein said treatment laser, said optical switch, said dosimetry detector, said optical sensing interrogator, and said DRS spectrometer are each multi-channeled in order to support a plurality of the fiber optic probes.

In a thirteenth embodiment, the present invention provides a system as in any of the tenth through twelfth embodiments, wherein each of said plurality of the fiber optic probes can be selectively controlled between performing treatment, monitoring a thermal ablation, and performing treatment and monitoring a thermal ablation.

In a fourteenth embodiment, the present invention provides a system as in any of the tenth through thirteenth embodiments, wherein said treatment laser provides treatment light to an optical switch for routing the treatment light to said treatment fiber.

In a fifteenth embodiment, the present invention provides a method of thermally ablating a tumor using the fiber optic probe as in any of the first through ninth or a system of the tenth through fourteenth embodiments, comprising the steps of identifying a tumor to be treated, obtaining an image of the tumor to be treated, and inserting the fiber optic probe into the tumor to be treated.

In a sixteenth embodiment, the present invention provides a method as in the fifteenth embodiment, wherein the step of obtaining is achieved by magnetic resonance imaging, computed tomography, or ultrasound imaging.

In a seventeenth embodiment, the present invention provides a method as in either of the fifteenth or sixteenth embodiments, further comprising the step of utilizing the obtained image to determine a predictive thermal model for treating the tumor to be treated.

In an eighteenth embodiment, the present invention provides a method as in any of the fifteenth through seventeenth embodiments, further comprising the step of inserting a plurality of the fiber optic probes into the tumor to be treated based on the predictive thermal model.

In a nineteenth embodiment, the present invention provides a method as in any of the fifteenth through eighteenth embodiments, wherein the tumor includes a margin between the tumor and the normal tissue, the method further comprising the step of providing treatment light to the tumor in order to thermally ablate the tumor, wherein the step of providing treatment light does not deleteriously damage the margin.

DETAILED DESCRIPTION OF ILLUSTRATIVE EMBODIMENTS

Embodiments of the present invention are based, at least in part, on a fiber optic probe capable of monitoring a thermal ablation procedure. Other embodiments of the present invention provide a fiber optic probe capable of both performing a thermal laser ablation procedure and monitoring the thermal laser ablation procedure. Other embodiments of the present invention relate to a method of using a plurality of fiber optic probes at different positions for optimal performance and monitoring of a thermal ablation procedure.

Figure 1:
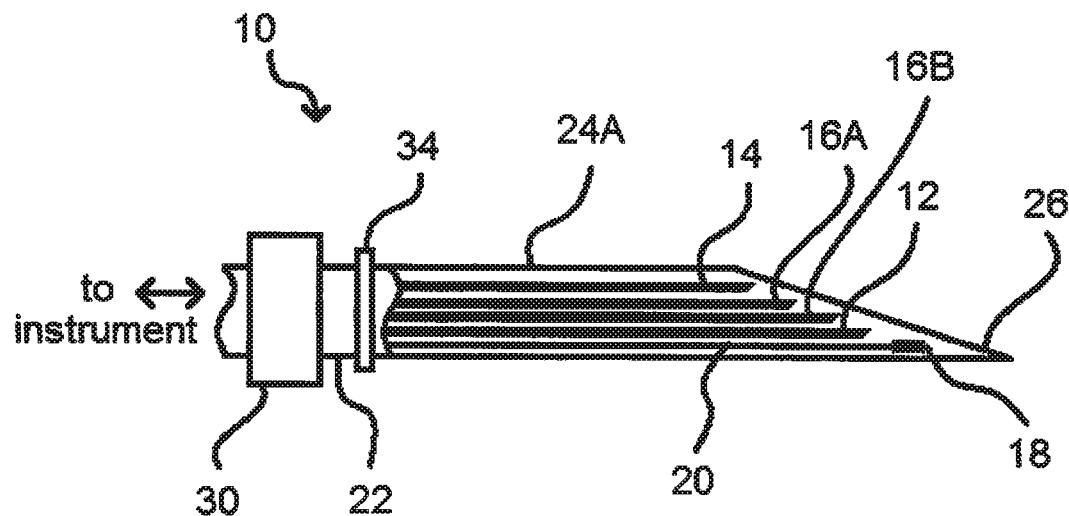
FIG. 1 is a schematic showing a cutaway side view of a probe having a needle shaped end according to embodiments of the invention.

With reference to FIG. 1, embodiments of the invention provide a probe, designated by the numeral 10, which may also be referred to as device 10, fiber optic sensor 10, or integrated laser-induced thermal therapy (i-LITT) device 10. In one or more embodiments, probe 10 may be suitable for use in vivo. Probe 10 includes a treatment fiber 12, a dosimetry fiber 14, two diffuse reflectance spectroscopy fibers 16A, 16B, and a temperature sensor 18 at a distal end of temperature sensor fiber 20. Treatment fiber 12, dosimetry fiber 14, diffuse reflectance spectroscopy fibers 16A, 16B, and temperature sensor fiber 20 may be provided in any suitable position with respect to each other. As used herein, treatment fiber 12, dosimetry fiber 14, diffuse reflectance spectroscopy fibers 16A, 16B, and temperature sensor fiber 20 may be collectively described as "the fibers" or as "the optical fibers."

Treatment fiber 12 is employed for delivering a high optical power density of light to the tumor. Dosimetry fiber 14 is employed for monitoring the light flux of the treatment fiber 12. Diffuse reflectance spectroscopy fibers 16A, 16B are employed for measuring the tissue optical properties. Temperature sensor 18 is employed for measuring local tissue temperatures.

At least a portion of treatment fiber 12, dosimetry fiber 14, two diffuse reflectance spectroscopy fibers 16A, 16B, and temperature sensor fiber 20 may be housed in a protective cable 22, which may also be referred to as protective coating 22, fiber optic jacket 22, or elongated sleeve 22, which extends into a distal end covering 24A, 24B. Protective cable 22 may be utilized to protect the fibers from damage, such as mechanical scratch or chemical or biological corrosion. In one or more embodiments, protective cable 22 may be made from polyvinyl chloride (PVC), polyethylene (PE), polyurethane (PUR), polybutylene terephthalate (PBT), polyamide (PA), and low smoke free of halogen (LSFH) materials.

As described above, protective cable 22 may extend into distal end covering 24A, 24B. As shown in FIG. 1, in one or more embodiments, distal end covering 24A is a needle shape having a sharp point 26. In these embodiments, probe 10 is suitable for use as a needle to be inserted through a layer, such as skin, and into a tumor. Other details regarding the use of probe 10 as a needle are generally known to those skilled in the art.

Figure 2:
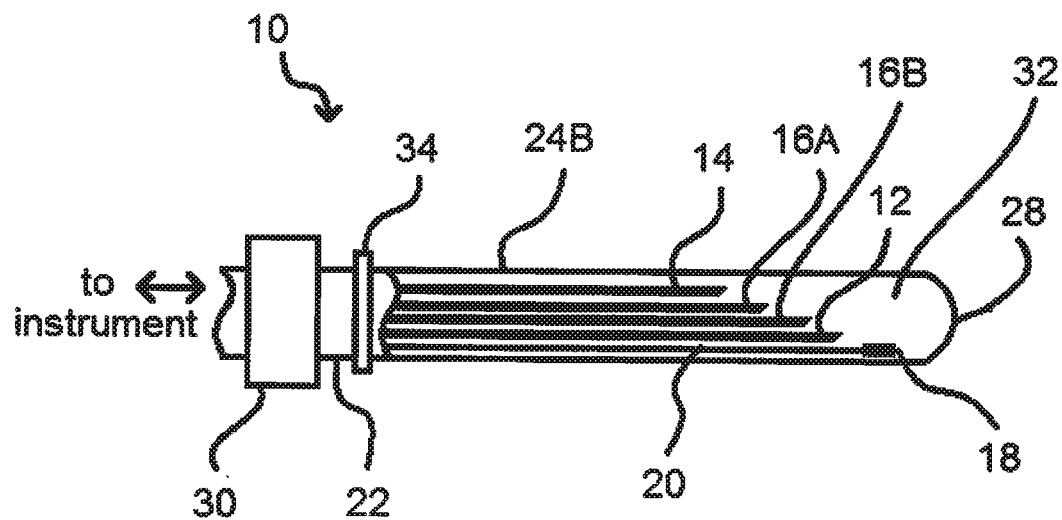
FIG. 2 is a schematic showing a cutaway side view of a probe having a rounded end according to embodiments of the invention.

As shown in FIG. 2, in one or more embodiments, distal end covering 24B includes a rounded distal end 28. Embodiments where probe 10 includes a rounded end are more particularly suited for use as a catheter to be inserted into a bodily cavity or a cannula. Other details regarding the use of probe 10 as a catheter are generally known to those skilled in the art.

Distal end covering 24A, 24B may be employed to protect the distal ends of the fibers from damage, such as mechanical scratch or chemical or biological corrosion. Distal end covering 24A, 24B may be made from a material suitable for the environment where probe 10 will be employed. In one or more embodiments, distal end covering 24A, 24B is made from a biocompatible material, such as biocompatible epoxy, as to not cause further harm to an in-contact tissue. In one or more embodiments, distal end covering 24A, 24B is formed of stainless steel. In one or more embodiments, distal end covering 24A, 24B is formed of a polymer that is transparent to all light in the visible and near-infrared band (400-1600 nm). Because it provides protection, in one or more embodiments, distal end covering 24A, 24B is strong enough that it does not deform under pressure utilized to insert probe 10 into a tumor.

Distal end covering 24A, 24B may be characterized by the size of the outer diameter or the gauge size. In one or more embodiments, distal end covering 24A, 24B has an outer diameter of 0.3 mm or more, in other embodiments, 0.5 mm or more, in other embodiments, 1.0 mm or more, in other embodiments, 1.5 mm or more, and in other embodiments, 2.0 mm or more. In one or more embodiments, distal end covering 24A, 24B has an outer diameter of 3.5 mm or less, in other embodiments, 3.0 mm or less, in other embodiments, 2.5 mm or more, in other embodiments, 2.0 mm or less, and in other embodiments, 1.5 mm or less.

In one or more embodiments, an adapter 30 may be utilized to couple together protective cable 22 with distal end covering 24A, 24B. Suitable adapters 30 for this function are generally known to those skilled in the art.

As shown in FIG. 2, one or more embodiments provide probe 10 having a fiber housing material 32 housing at least a distal end of the fibers. This may also be described as at least a distal end of the fibers being embedded in fiber housing material 32. In one or more embodiments, fiber housing material 32 is a biocompatible optical epoxy. Fiber housing material 32 may be formed of any polymer that is transparent to all light in the visible and near-infrared band (400-1600 nm). Fiber housing material 32 may fixedly secure the fibers in position in probe 10 such that the relative distances among all fiber tips are maintained.

Figure 4:
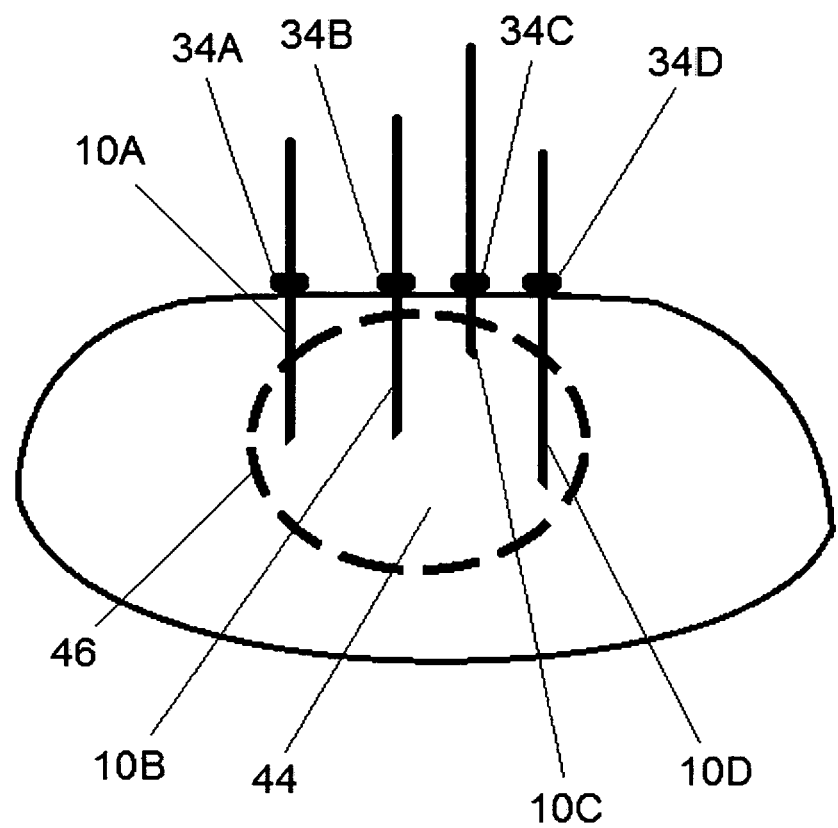
FIG. 4 is a schematic showing a plurality of probes utilized to ablate and monitor a tumor according to embodiments of the invention.

As shown in FIGS. 1 and 2, one or more embodiments provide a probe 10 having a stopper 34 circumferentially positioned around distal end covering 24A, 24B. As will be discussed further herein below, and as shown in FIG. 4 for a plurality of probes 10, stopper 34 may be longitudinally adjustable with respect to distal end covering 24A, 24B in order to position probe 10 at a predetermined location. Stopper 34 is adapted to contact the outer layer, such as the skin, in order to temporarily fix probe 10 in position.

Embodiments of the invention provide a probe 10 capable of both thermal ablating a tumor by way of treatment fiber 12 and monitoring the thermal ablation by way of dosimetry fiber 14, diffuse reflectance spectroscopy fibers 16A, 16B, and temperature sensor 18 at a distal end of temperature sensor fiber 20. Embodiments of the invention where probe 10 is capable of both thermal ablating a tumor by way of treatment fiber 12 and monitoring the thermal ablation by way of dosimetry fiber 14, diffuse reflectance spectroscopy fibers 16A, 16B, and temperature sensor 18 at a distal end of temperature sensor fiber 20 can be utilized within a method where probe 10 selectively ablates and monitors, or just ablates, or just monitors, based on an optimized thermal ablation.

One or more embodiments provide a probe without a treatment fiber such that the probe is only capable of monitoring a thermal ablation by way of dosimetry fiber 14, diffuse reflectance spectroscopy fibers 16A, 16B, and temperature sensor 18 at a distal end of temperature sensor fiber 20. One or more embodiments provide a probe without dosimetry fiber 14, such that the probe may be only capable of monitoring a thermal ablation by way of diffuse reflectance spectroscopy fibers 16A, 16B and temperature sensor 18 at a distal end of temperature sensor fiber 20. These embodiments where a probe is without a treatment fiber would preferably be utilized with another energy treatment, such as radio waves or microwaves, which are generally known to those skilled in the art. As will be further described herein below, embodiments of the invention provide a probe capable of monitoring temperature, laser flux, tissue optical properties, tissue absorption, reduced scattering coefficients, and combinations thereof.

In one or more embodiments, treatment fiber 12 is an optical fiber employed to deliver light to a tumor. The light may also be referred to as high optical power density of light. This delivery of light may also be referred to as laser interstitial thermal therapy (LITT). The light may be either continuous or pulsed. In one or more embodiments, the light may be infrared laser. In one or more embodiments, the light may be near-infrared laser. In one or more embodiments, the light may be Nd:YAG or diode laser. In one or more embodiments, the light may be in a wavelength of from 800 nm to 1064 nm.

In one or more embodiments, treatment fiber 12 is a side-firing fiber. In one or more embodiments, treatment fiber 12 is a forward-firing fiber with a diffuser (not shown) at the tip. The treatment of a tumor using treatment fiber 12 may be as part of a minimally-invasive procedure, such as percutaneous or endovenous. Other details regarding treatment fiber 12 and LITT, including exemplary treatment fibers suitable for use, are generally known to those skilled in the art.

When treating a tumor with treatment fiber 12, the heat generated due to the local absorption of light depends on the light fluence rate (W/cm$^2$) and the optical absorption and scattering properties of the tissue. Therefore, the light penetration and volume of coagulation during LITT can be determined by the scattering and absorption properties of the tumor. In addition, tissue optical properties are wavelength dependent; implying that, for a given tumor, the volume and depth of ablation could vary depending on the laser ablation wavelength. The light fluence rate may be varied based on the tissue type and tumor volume.

When using LITT to treat a tumor, the laser of treatment fiber 12 may be used to target the light absorption by water, lipid, hemoglobin, or combinations thereof. Most tumors are highly vascularized which can denote a higher hemoglobin content within the tumor mass. In one or more embodiments, the laser of treatment fiber 12 may be provided with a wavelength (e.g. 980 nm) in order to target the absorption of water and hemoglobin for a predetermined amount of time. In one or more embodiments, the laser of treatment fiber 12 may be provided with a wavelength (e.g. 1064 nm) in order to target the absorption of water for a predetermined amount of time. The targeting of hemoglobin and water absorption generally induces thermo-coagulation. For laser ablation, the distribution of the light from treatment fiber 12 generally changes with changing tissue optical properties under the influence of heating. For this reason, the total energy or laser power delivered to the tissue should be updated constantly depending upon the laser penetration depth.

During thermal ablation, such as LITT, of a tumor, the temperature distribution within the tissue depends on the energy absorbed by target tissue, energy-to-heat converting efficiency, thermal conductivity, and perfusion of the tissue. As discussed in the background section, it is known that thermal therapy creates three different zones of hyperthermic ablation in the target tissue: a first zone (Zone 1) including the area surrounding the applicator tip; a second zone (Zone 2) immediately next to Zone 1 having a steep negative temperature-gradient, called the peripheral gradient or transitional zone; and a third zone (Zone 3) of tissue beyond Zone 2 serving as a heat-sink to the other zones due to the blood perfusion. Embodiments of the present invention provide an effective treatment where a whole tumor is completely coagulated without tissue charring. That is, embodiments of the invention are able to keep the tumor mass completely covered in Zone 1. In these or other embodiments, the damage to the normal tissue is minimized. This may also be described with respect to the tumor margin, which is the transition area between the tumor and the normal tissue. In one or more embodiments, the tumor margin is maintained within Zone 2 of a thermal ablation. As will be discussed herein below, embodiments of the invention may utilize multiple applicators, particularly for complete ablation of larger tumors (>3 cm).

Probe 10 having treatment fiber 12 may be used to thermally treat a variety of tissues, such as bone, brain, liver, lung, kidney, and prostate.

In one or more embodiments, dosimetry fiber 14 is an optical fiber employed to collect light. This may also be described as dosimetry fiber 14 monitoring the light flux of the treatment fiber 12. In one or more embodiments, dosimetry fiber 14 is a side-firing fiber. Dosimetry fiber 14 and the dosimetry detector operatively coupled therewith, which will be described herein below, are able to collect and measure light from treatment fiber 12 in order to determine the local light fluence rate of the treatment laser. If the light collected by dosimetry fiber 14 is lower, this can be an indication that there is either too low light output from treatment fiber 12 or that the tumor is absorbing a significant portion of the light from treatment fiber 12. The light absorbed generally depends on the tumor absorption and scattering properties. The light absorbed also generally varies with heating because heating changes the tissue optical properties. Other details regarding dosimetry fibers, including exemplary dosimetry fibers suitable for use, are generally known to those skilled in the art.

Light propagation within a tissue is generally dependent on the tissue microstructure and physiology. The light scattering is sensitive to changes in tissue microstructure, while light absorption is dependent on the distribution of chromophores within the tissue. Thus, one or more embodiments provide continuous monitoring of changes in tissue absorption and scattering properties in order to assist in assessing the tissue status during an ablation procedure to achieve a desired treatment endpoint. This may include observing differences in tissue absorption ($\mu_a(\lambda)$) and scattering coefficients ($\mu_s'(\lambda)$) of native and coagulated tissues.

In one or more embodiments, a first diffuse reflectance spectroscopy (DRS) fiber 16A and a second diffuse reflectance spectroscopy fiber 16B are employed to quantify the tissue $\mu_a(\lambda)$ and $\mu_s'(\lambda)$ in vivo. As used herein, first diffuse reflectance spectroscopy fiber 16A and second diffuse reflectance spectroscopy fiber 16B may be collectively described as "the DRS fibers." The DRS fibers are able to continuously quantify changes in tissue optical absorption and scattering properties, and can thereby be used as a diagnostic biomarker for assessing tissue coagulation or damage during thermal ablation. In one or more embodiments, the DRS fibers are side-firing fibers.

First diffuse reflectance spectroscopy fiber 16A, which may also be referred to as source fiber 16A, is operatively coupled with a light source in order to provide light into a target or tissue for quantification. In one or more embodiments, the light source may be a white light-emitting-diode (LED), a thermal lamp, an LED, or a laser diode (LD), so long as the light source provides a broad spectrum useful for DRS.

A separation gap is provided between first diffuse reflectance spectroscopy fiber 16A and a second diffuse reflectance spectroscopy fiber 16B, which may also be referred to as detection fiber 16B. The separation gap allows the light to sufficiently scattered or absorbed before being received by second diffuse reflectance spectroscopy fiber 16B. Second diffuse reflectance spectroscopy fiber 16B is employed to detect the reflective light and is operatively coupled with a spectrometer for calculating the detected light. Thus, first diffuse reflectance spectroscopy fiber 16A and second diffuse reflectance spectroscopy fiber 16B are able to perform DRS measurement of the tissue optical properties. One or more additional aspects of the DRS fibers, or other features disclosed herein, may be generally disclosed in PCT Publication No. WO 2016/019235 and U.S. Publication No. US 2016/0045102, which are incorporated herein by reference.

The change in tissue microstructure and physiology during heating alters the propagation of light within the tissue. These alterations are manifested through changes in the tissue $\mu_a(\lambda)$ and $\mu_s'(\lambda)$. The light from first diffuse reflectance spectroscopy fiber 16A is scattered within a biological tissue, such as by contacting mitochondria, cell nuclei, cell membranes, or other tissue components. Second diffuse reflectance spectroscopy fiber 16B detects the scattered light and sends this detection to the spectrometer in order to measure scattering.

Tissue scattering is affected by the refractive index mismatch at the membrane boundary. This boundary changes during heating due to rupturing of cell membranes, coagulation of structural proteins, loss of extracellular fluids, or formation of new particles. Changes in absorption may be due to denaturation of chromophores and tissue shrinkage. The present invention may help to understand the temperature-dependent absorption of major tissue chromophores.

In one or more embodiments, temperature sensor 18 is employed at a distal end of an optical fiber, which may be described herein as temperature sensor fiber 20. In one or more embodiments, temperature sensor 18 is an interferometric fiber optic sensor. An exemplary interferometric fiber optic sensor is a Fabry-Perot interferometer (FPI sensor). Temperature sensor 18 is employed to monitor the temperature of the tissue and tumor.

Figure 5:
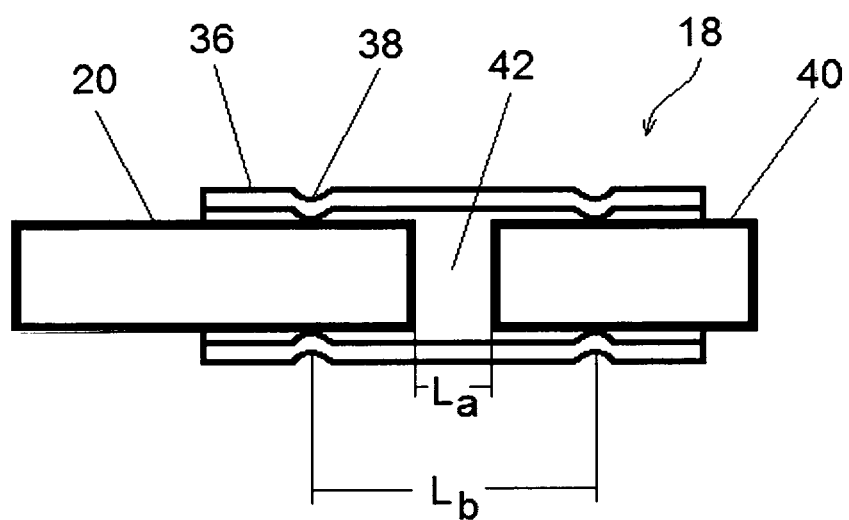
FIG. 5 is a schematic showing a sectional view of an exemplary temperature sensor.

With reference to FIG. 5, temperature sensor 18 includes a capillary tube 36 secured to temperature sensor fiber 20, such as by way of a laser fusion bond 38. Capillary tube 36 is also secured to a dead end fiber 40, and provides a cavity 42 between temperature sensor fiber 20 and dead end fiber 40 having a cavity length $L_a$. Capillary tube 36 may be made from borosilicate. Capillary tube 36 may have an outer diameter of 400 µm or approximate thereto. In one or more embodiments, temperature sensor fiber 20 and dead end fiber 40 are multi-mode fibers.

Temperature sensor 18 calculates the temperature by measuring changes in cavity length $L_a$ due to thermal expansion of capillary tube 36. At temperature T, the change in $L_a$ from $T_0$ is given by $\Delta L_a=(\alpha_b-\alpha_f)(T-T_0)L_b$, where $\alpha_b$ and $\alpha_f$ are the coefficients of thermal expansion (CTE) of capillary tube 36 and temperature sensor fiber 20, respectively, and where $L_b$ is the gauge length of capillary tube 36. By measuring the cavity length $L_a$ using low-coherence interferometry, the tissue temperature T can be determined. By choosing the right combination of initial cavity length $L_a$ and gauge length of capillary tube 36 ($L_b$) at room temperature $T_0$, a desired measuring temperature range can be achieved. In one or more embodiments, temperature sensor 18 has a measuring temperature range of from 20° to 100° C. In one or more embodiments, temperature sensor 18 has an accuracy of plus or minus 1° C. within a measuring temperature range of from 20° to 100° C. In addition, temperature drift, hysteresis, repeatability, and sensitivity of temperature sensor 18 may be optimized.

The optical fibers used for treatment fiber 12, dosimetry fiber 14, diffuse reflectance spectroscopy fibers 16A, 16B, and temperature sensor fiber 20 are generally known to those skilled in the art, and may include a core, cladding, and coating. The core of an optical fiber may be a cylinder of glass or plastic that runs along a fiber's length. The core may be surrounded by a medium with a lower index of refraction, typically a cladding of a different glass, or plastic. Light travelling in the core reflects from the core-cladding boundary due to total internal reflection, as long as the angle between the light and the boundary is less than the critical angle. As a result, a fiber transmits all rays that enter the fiber with a sufficiently small angle to the fiber's axis. The limiting angle is called the acceptance angle, and the rays that are confined by the core/cladding boundary are called guided rays. The cladding may be surrounded by a coating, which may be a layer, or multi-layers, of plastic. The coating may be employed to preserve fiber strength, absorb shock and provide extra fiber protection. The optical fibers may include any suitably sized outer diameter of the core, cladding, and coating.

The optical fibers may be characterized by the angle of the tip. In one or more embodiments, a fiber has a tip at a 45 degree angle, or approximate thereto, with respect to the fiber axis, as shown in FIGS. 1 and 2. In one or more embodiments, a fiber has a tip at a 90 degree angle, or approximate thereto. In order to achieve a tip having a 45 degree angle, or approximate thereto, the tip may be polished to achieve the angled tip.

In one or more embodiments, the optical fibers may include a mirror coating, which may be employed to bend the source or detected light path by 90 degrees. An exemplary mirror coating is a metal coating, such as a gold coating. As described above, the optical fibers may be housed in a fiber housing material. Prior to adding the fiber housing material to fixedly secure the optical fibers, the optical fibers may be held in place by an internal disc.

The optical fibers may be characterized by the type of paths that the light rays, or modes, travel within the fiber core. In one or more embodiments, a fiber may be characterized as a multimode fiber. In one or more embodiments, a multimode fiber may be characterized as a step index fiber. In one or more embodiments, a multimode fiber may be characterized as a graded index fiber. In one or more embodiments, a fiber may be characterized as a single-mode fiber.

Any of the above characterizations of "a fiber" or "the optical fibers" may be applied to each of treatment fiber 12, dosimetry fiber 14, diffuse reflectance spectroscopy fibers 16A, 16B, and temperature sensor fiber 20. In one or more embodiments, temperature sensor fiber 20 is a multimode fiber and treatment fiber 12, dosimetry fiber 14, and diffuse reflectance spectroscopy fibers 16A, 16B are large core single-mode fibers.

Figure 3:
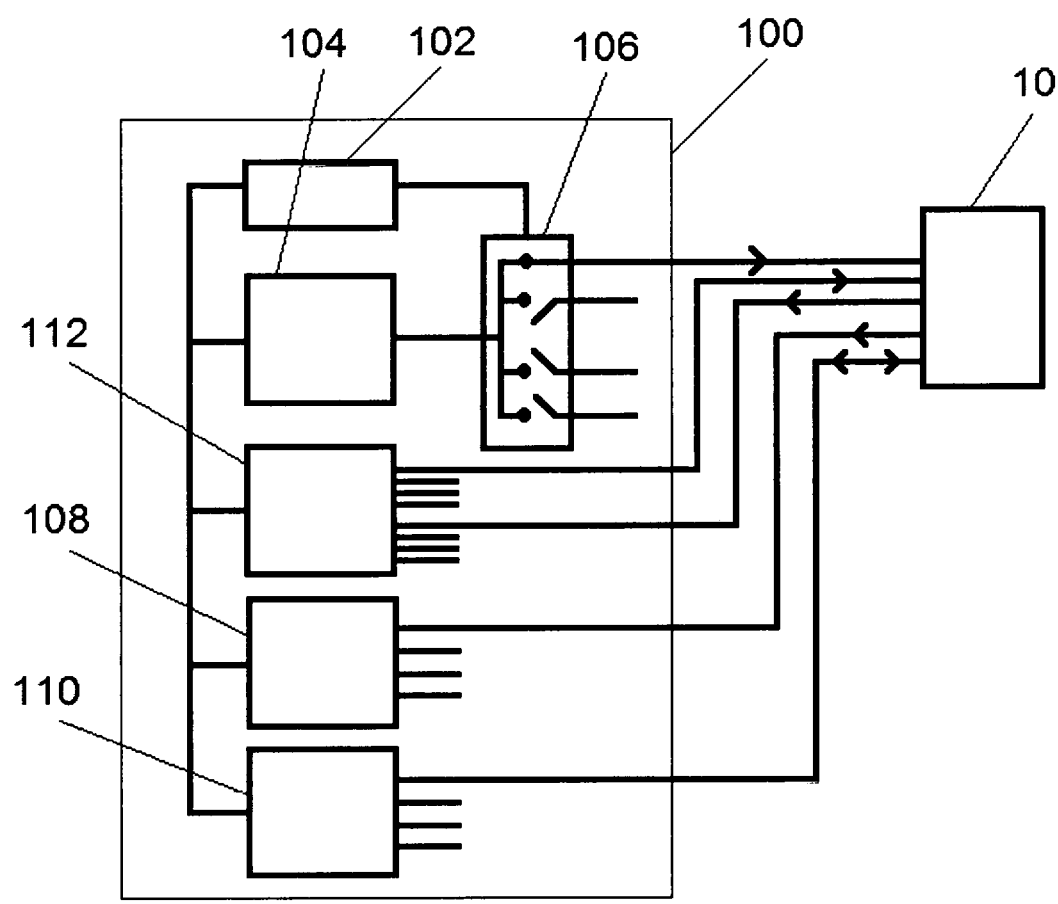
FIG. 3 is a schematic showing an instrument for coupling with a probe for operating probe according to embodiments of the invention.

With reference to FIG. 3, embodiments of the invention employ probe 10 operatively coupled with an instrument 100 for operating probe 10. Instrument 100 includes a computer 102 in operative communication, either wirelessly or hardwired, with a treatment laser 104, an optical switch 106, a dosimetry detector 108, an optical sensing interrogator 110, and a DRS spectrometer 112. This operative communication may also be described as operatively coupled in one or more embodiments.

In one or more embodiments, as seen in FIG. 3, optical switch 106, dosimetry detector 108, optical sensing interrogator 110, and DRS spectrometer 112 may be multi-channeled in order to support a plurality of probes 10. That is, a first probe may be used with a first channel, a second probe may be used with a second channel, and so on. Although FIG. 3 particularly shows four channels, it should be appreciated that any suitable number of channels may be utilized. In one or more embodiments, instrument 100 includes one channel, in other embodiments, two channels, in other embodiments, three channels, in other embodiments, four channels, in other embodiments, five channels, and in other embodiments, six channels.

Computer 102 is generally known to those skilled in the art and may include custom software to control all the components and to analyze the measured data. Computer 102 includes a microprocessor that together with appropriate software, hardware, firmware, and the like, is able to control the components and to analyze the measured data through known methods. One skilled in the art will know how to implement suitable software for controlling and analyzing. In one or more embodiments, computer 102 is a laptop computer.

In one or more embodiments, computer 102 may be used to selectively utilize treatment laser 104, optical switch 106, dosimetry detector 108, optical sensing interrogator 110, and DRS spectrometer 112. That is, treatment laser 104 and the monitoring modules (e.g dosimetry detector 108, optical sensing interrogator 110, and DRS spectrometer 112) may be controlled independently and powered on and off independently.

Thus, in embodiments utilizing a single probe 10, a probe 10 having both treatment fiber 12 and monitoring fibers (e.g. dosimetry fiber 14, diffuse reflectance spectroscopy fibers 16A, 16B, and temperature sensor fiber 20) may be selectively controlled as to only treat via treatment fiber 12 or to only monitor via monitoring fibers or to both treat and monitor. In embodiments utilizing a plurality of probes 10, each probe 10 may be selectively controlled as to only treat via treatment fiber 12 or to only monitor via monitoring fibers or to both treat and monitor. Each probe 10 may also be selectively turned off as to neither treat nor monitor. This selectivity allows for more optimal treatment and monitoring of a thermal ablation procedure.

Practice of the present invention is not limited to any particular computer 102, treatment laser 104, optical switch 106, dosimetry detector 108, optical sensing interrogator 110, and DRS spectrometer 112. Exemplary treatment laser 104, optical switch 106, dosimetry detector 108, optical sensing interrogator 110, and DRS spectrometer 112 and details thereof are generally known to those skilled in the art.

Treatment laser 104 provides treatment light to treatment fiber 12. In one or more embodiments, treatment laser 104 may be a high power treatment laser. Treatment laser 104 may provide either continuous laser or pulsed laser.

The treatment light from treatment laser 104 may be passed to optical switch 106 for routing the input treatment light to an output channel for routing the treatment light to treatment fiber 12. Where a plurality of probes 10 are provided, optical switch 106 may include the same number of output channels as probes 10. As described herein, optical switch 106 may selectively provide the input treatment light to certain of the output channels. FIG. 3 shows a 1×4 optical switch 106, that is, one input and four outputs, but any suitable number of inputs or outputs may be utilized.

The treatment light collected by dosimetry fiber 14 is provided back to dosimetry detector 108. Dosimetry detector 108 may also detect, amplify, and digitize the collected treatment light. Where a plurality of probes 10 are provided, dosimetry detector 108 may include the same number of input channels as probes 10. As described herein, dosimetry detector 108 may selectively detect the collected treatment light. FIG. 3 shows four inputs, but any suitable number of inputs may be utilized.

Optical sensing interrogator 110 is employed to measure the temperature using temperature sensor 18 and temperature sensor fiber 20. In one or more embodiments, optical sensing interrogator 110 employs a tunable laser paired with a photodetector. An exemplary photodetector is sm125-500 from Micron Optics, Inc. in Atlanta, Ga. In one or more embodiments, optical sensing interrogator 110 employs an LED or SLED paired with a spectrometer. Optical sensing interrogator 110 is able to measure the temperature by collecting the changes in cavity length $L_a$, as described above. Where a plurality of probes 10 are provided, optical sensing interrogator 110 may include the same number of input channels as probes 10. Where a plurality of probes 10 are utilized, the temperatures may be collected either in parallel or sequentially. As described herein, optical sensing interrogator 110 may selectively detect the temperature. FIG. 3 shows four inputs, but any suitable number of inputs may be utilized.

DRS spectrometer 112 is employed to detect the diffuse reflectance spectrum collected by second diffuse reflectance spectroscopy fiber 16B. In one or more embodiments, the collected diffuse reflectance spectrum is analyzed by an algorithm. The reflectance spectrum is analyzed through known techniques using a model of photon propagation in tissue (e.g., diffusion equation, Monte Carlo simulation or empirical model) to extract the absorption and reduced scattering coefficients. From the absorption spectrum, the concentrations of the absorbers (such as oxy-hemoglobin, deoxy-hemoglobin, beta-carotene and melanin, etc.) can be computed using the Beer-Lambert law (also known as Beer's law). The scattering reflects the tissue morphological information, such as nuclear size and density. Both tissue compositions and morphological information have been identified as useful biomarkers for cancer diagnostics. Where a plurality of probes 10 are provided, DRS spectrometer 112 may include the same number of input channels as probes 10. As described herein, DRS spectrometer 112 may selectively detect the collected diffuse reflectance spectrum. FIG. 3 shows four inputs, but any suitable number of inputs may be utilized.

As described above, one or more embodiments provide a probe without a treatment fiber. Thus, embodiments provide an instrument having only dosimetry detector 108, optical sensing interrogator 110, and DRS spectrometer 112. Other embodiments provide an instrument having only optical sensing interrogator 110 and DRS spectrometer 112.

The present invention also provides methods for determining optimal tumor ablation. To ensure complete tumor ablation, currently known practices ablate a small margin of surrounding normal tissues, in addition to the target tumor tissue. However, these known methods may lead to tissue charring and may not be feasible when tumors are near critical structures such as major nerves, blood vessels or organs. Embodiments of the present invention provide continuous monitoring of a thermal ablation process in order to achieve complete and optimal tumor ablation.

As will be discussed further herein, embodiments of the invention provide methods of monitoring a thermal ablation procedure including a step of image-guidance. This image-guidance may be used to locate the tumor and to determine optimal placement of probes 10. An additional step of image-guidance during or following thermal ablation may provide an assessment of the thermal damage to the target tissue.

In one or more embodiments, a method includes a step of estimating the thermal tissue damage by measuring tissue temperature and using the Arrhenius damage integral (Equation 1).

$$\Omega_A = \ln\left(\frac{c(0)}{c(t)}\right) = \int_0^\tau A e^{\frac{(-E_a)}{(RT(t))}} dt \qquad \text{Equation 1}$$

In Equation 1, $\Omega_A$ is the Arrhenius tissue damage index, A is the Arrhenius exponential factor, $E_a$ is the activation energy, t is the duration of heating, R is the gas constant, T is the temperature in Kelvin, c(0) is the concentration of the native molecules and c(t) is the concentration of denatured molecules. $E_a$ and A are tissue specific and may be experimentally determined. The percentage of denatured tissue, $F_d$ can be derived from Equation 1 using the below Equation 2. A tissue coagulation process involves more than one molecular species and ideally $\Omega_A$ must be taken into account to represent the total tissue damage. This Arrhenius model assumes tissue coagulation to be a unimolecular reaction in order to estimate $\Omega_A$.

$$F_d = 1 - e^{-\Omega_A} = \frac{c(t) - c(0)}{c(0)} \qquad \text{Equation 2}$$

Using Equation 1 and Equation 2, an $F_d=1$ signifies complete denaturation whereas $F_d=0$ indicates no thermal denaturation or native tissue. Based on Equation 1 and Equation 2, it should be appreciated that certain embodiments utilize only temperature and duration of heating to determine $\Omega_A$ and $F_d$. In one or more embodiments, a method includes achieving $F_d=1$ without causing tissue charring.

Temperature-based estimation of tissue damage is an indirect method for assessing the degree of damage. During a coagulation process, tissues undergo both microscopic and macroscopic changes in their structures and physiological functions. Thus, embodiments of the invention are able to monitor these changes in order to achieve a more direct approach to assess the extent of thermal damage. As described herein, quantitative diffuse reflectance spectroscopy (DRS) is a non-destructive method that is sensitive to tissue absorption and scattering, and thus can be used to quantify the tissue morphological and physiological properties in vivo. The light scattering is sensitive to changes in tissue microstructure, while light absorption is dependent on the distribution of chromophores within a tissue. Embodiments of the invention include continuous monitoring of changes in tissue absorption and scattering properties in order to assess the tissue status during an ablation procedure to achieve a desired treatment endpoint.

As described herein, probe 10 and associated methods of use are able to monitor certain parameters of a thermal ablation procedure. In one or more embodiments, probe 10 may monitor tumor temperature, tissue temperature, tissue optical properties, such as tissue light absorption, reduced scattering coefficients, laser flux, or combinations thereof.

Embodiments of the present invention include methods for determining the accuracy of probe 10. Certain embodiments include determining the accuracy of probe 10 by calibrating probe 10. Certain embodiments include determining the accuracy of probe 10 by utilizing the probe in a phantom tissue experiment.

In one or more embodiments, a method of calibrating probe 10 includes using probe with a phantom tissue experiment. A phantom tissue is a material designed to simulate a tissue in order to mimic light propagation in a living tissue. Because the particular properties of a phantom tissue are known, an experiment using a phantom tissue may be used to determine the accuracy of probe 10. If an experiment using a phantom tissue reveals an inaccuracy of probe 10, probe 10 or the results obtained therefrom may be correspondingly adjusted. An exemplary phantom tissue includes a mixture of water with human Hemoglobin (Hb) powder (H0267, Sigma-Aldrich Co. LLC) as the absorber and 1-μm Polystyrene beads (07310-15, Polysciences Inc.) as the tissue scatterer. A number of phantom tissues may be prepared covering a wide range of hemoglobin concentrations. Then probe 10 may be used to determine diffuse reflectance spectrum for each of the phantoms in order to compare these results to those obtained by a spectrophotometer.

Embodiments of the invention provide methods of utilizing probe 10 to treat a tumor. These methods may utilize a single probe 10 or a plurality of probes 10. Methods utilizing a single probe may be particularly suitable for treating tumors having a size smaller than 3 cm. Methods utilizing a plurality of probes may be particularly suitable for treating tumors sized greater than 3 cm.

In one or more embodiments, a method includes a step of identifying a tumor to be treated. Then, the tumor may be imaged in order to provide details about the tumor and surrounding tissue. This may also be referred to as an image-guidance step. An image obtained in an image-guidance step may be either a 2-D image or a 3-D image. Exemplary techniques for performing an image-guidance step may include MRI, CT, or ultrasound imaging. An image-guidance step may determine tumor size, tumor shape, vasculatures, thermal conductivity distribution, or combinations thereof.

Following an image-guidance step, a subsequent step may include utilizing the information obtained in the image-guidance step to assist with a thermal ablation. The obtained information may be fed into a predictive thermal model that determines the number of probes and their optimal locations. One skilled in the art will generally know how to obtain and utilize the predictive thermal model.

Embodiments of the invention include a further step of inserting a probe, or a plurality of probes, into a tumor. This insertion may be done using the image-guidance and information and predictive model. In one or more embodiments, a method includes delivering the high power laser to the distal end of the probes, which may be either sequentially or scanned in embodiments utilizing multiple probes. The high power laser then enables thermal ablation of the tumor.

Embodiments of the invention include a step of monitoring the thermal ablation. One or more monitoring channels may be turned on prior to, concurrently with, or following the delivering of the treatment, such as the high power laser. In one or more embodiments, all monitoring channels, that is, dosimetry, DRS, and temperature sensor, in all probes are turned on in order to continuous monitor the thermal ablation parameters. As discussed herein, the information from the monitoring channels may be analyzed by a computer, which may include custom software. These analyses may be to evaluate the tissue status, such as the degree of coagulation or damage, and to subsequently adjust the power and duration of the treatment laser to a probe or to each of a plurality of probes.

As discussed above, one or more embodiments provide a method wherein the tumor margin is maintained within Zone 2 of a thermal ablation. One or more embodiments provide a method utilizing an optimal temperature distribution in order to ensure complete destruction of tumor mass. This may reduce recurrence rate, while avoiding tissue charring and excessive damage to normal tissue.

With particular respect to FIG. 4, following a step of utilizing a predictive thermal model as discussed above, the predictive model may be used to determine the optimal position for a plurality of probes 10. For instance, a first probe 10A having both treatment and monitoring capabilities may be inserted into a first location and at a first depth in tumor 44. This may include adjusting a first stopper 34A to a predetermined position. In the same way, a second probe 10B having both treatment and monitoring capabilities may be inserted into a second location and at a second depth in tumor 44, which may include adjusting a second stopper 34B to a predetermined position. Additional probes, such as a third probe 10C and a fourth probe 10D may also be provided at additional locations and depths in tumor 44, and a third stopper 34C and a fourth stopper 34D may be likewise adjusted. Probes 10A, 10B, 10C, and 10D are as described herein with respect to probe 10 and stoppers 34A, 34B, 34C, and 34D are as described herein with respect to stopper 34. In one or more embodiments, probes 10A, 10B, 10C, and 10D are needle shaped.

Following the insertion of a plurality of probes in tumor 44, a treatment laser may be provided to each of the probes. Also, each of the probes may monitor the thermal ablation. The positioning of the plurality of probes enables the thermal ablation of tumor 44 to proceed to completion without significant tissue damage or scarring. That is, the damages to the normal tissue on the tumor margin 46 may be minimized.

In one or more embodiments, first probe 10A is a treatment-mode probe that may be utilized to thermally treat a tumor and second probe 10B is a monitoring-mode that may be utilized to monitor the thermal treatment. The treatment-mode and monitoring-mode are as described herein with respect to selectively utilizing treatment and monitoring, respectively, for a probe. Any suitable number of treatment-mode probes and any suitable number of monitoring-mode probes may be utilized.

In light of the foregoing, it should be appreciated that the present invention advances the art. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A fiber optic probe comprising a plurality of fibers, the plurality of fibers comprising
a first diffuse reflectance spectroscopy fiber,
a second diffuse reflectance spectroscopy fiber,
wherein said first diffuse reflectance spectroscopy fiber is a source fiber operatively coupled with a light source in order to provide light from said light source to a tumor to thereby become scattered light,
wherein said second diffuse reflectance spectroscopy fiber is a detection fiber for detecting said scattered light,
a temperature sensor fiber,
said temperature sensor fiber having a temperature sensor at a distal end thereof,
wherein said temperature sensor is an interferometric fiber optic sensor,
a treatment fiber for delivering laser light having a light flux and a wavelength of from 800 nm to 1064 nm to said tumor, and
a dosimetry fiber for monitoring said light flux.

2. The fiber optic probe of claim 1, wherein said light source is a white light-emitting-diode and wherein said second diffuse reflectance spectroscopy fiber is operatively coupled with a spectrometer for calculating the scattered light.

3. The fiber optic probe of claim 1, wherein said first diffuse reflectance spectroscopy fiber, said second diffuse reflectance spectroscopy fiber, said temperature sensor fiber, said treatment fiber, and said dosimetry fiber are optical fibers.

4. The fiber optic probe of claim 1, further comprising a protective cable housing at least a portion of each of said first diffuse reflectance spectroscopy fiber, said second diffuse reflectance spectroscopy fiber, said temperature sensor fiber, said treatment fiber, and said dosimetry fiber, said protective cable extending into a distal end covering housing a distal end of each of said first diffuse reflectance spectroscopy fiber, said second diffuse reflectance spectroscopy fiber, said temperature sensor fiber, said treatment fiber, and said dosimetry fiber.

5. The fiber optic probe of claim 4, said distal end covering being in the shape of a needle and being made from stainless steel.

6. The fiber optic probe of claim 4, said distal end covering including a rounded distal end and being made from biocompatible epoxy.

7. The fiber optic probe of claim 4, the distal end covering having an outer diameter of from 0.3 mm to 2.0 mm.

8. The fiber optic probe of claim 7, the distal end covering having a stopper circumferentially positioned therearound.

9. A system comprising the fiber optic probe of claim 1, wherein said first diffuse reflectance spectroscopy fiber and said second diffuse reflectance spectroscopy fiber are operatively coupled with a diffuse reflectance spectroscopy spectrometer, said temperature sensor fiber is operatively coupled with an optical sensing interrogator, said treatment fiber is operatively coupled with a treatment laser, and said dosimetry fiber is operatively coupled with a dosimetry detector.

10. The system of claim 9, further comprising a computer operatively coupled with said treatment laser, said optical switch, said dosimetry detector, said optical sensing interrogator, and said diffuse reflectance spectroscopy spectrometer.

11. The system of claim 10, wherein said treatment laser, said optical switch, said dosimetry detector, said optical sensing interrogator, and said diffuse reflectance spectroscopy spectrometer are each multi-channeled in order to support a plurality of the fiber optic probes of claim 1.

12. The system of claim 11, wherein each of said plurality of the fiber optic probes can be selectively controlled between performing treatment, monitoring a thermal ablation, and performing treatment and monitoring a thermal ablation.

13. The system of claim 9, wherein said treatment laser provides treatment light to an optical switch for routing the treatment light to said treatment fiber.

14. A method of thermally ablating a tumor using the fiber optic probe of claim 1, comprising steps of identifying a tumor to be treated, obtaining an image of the tumor to be treated, and inserting the fiber optic probe into the tumor to be treated.

15. The method of claim 14, wherein the step of obtaining is achieved by magnetic resonance imaging, computed tomography, or ultrasound imaging.

16. The method of claim 14, further comprising a step of utilizing the obtained image to determine a predictive thermal model for treating the tumor to be treated.

17. The method of claim 16, further comprising a step of inserting a plurality of the fiber optic probes of claim 1 into the tumor to be treated based on the predictive thermal model.

18. The method of claim 17, wherein the tumor includes a margin between the tumor and the normal tissue, the method further comprising a step of providing treatment light to the tumor in order to thermally ablate the tumor, wherein the step of providing treatment light does not deleteriously damage the margin.

19. The fiber optic probe of claim 1, wherein the plurality of fibers consists of the first diffuse reflectance spectroscopy fiber, the second diffuse reflectance spectroscopy fiber, the temperature sensor fiber, the treatment fiber, and the dosimetry fiber.

20. The fiber optic probe of claim 19, the fiber optic probe further comprising a distal end covering housing a distal end of each of the plurality of fibers, the distal end covering having an outer diameter of from 0.3 mm to 2.0 mm.

* * * * *